United States Patent [19]
Yurchak

[11] Patent Number: 4,814,535
[45] Date of Patent: Mar. 21, 1989

[54] CONVERSION OF OXYGENATES TO GASOLINE AT VARIABLE INLET TEMPERATURE

[75] Inventor: Sergei Yurchak, Media, Pa.

[73] Assignee: Mobil Oil Corporation, New York, N.Y.

[21] Appl. No.: 133,415

[22] Filed: Dec. 15, 1987

[51] Int. Cl.$^4$ ............................................. C07C 11/20
[52] U.S. Cl. .................................. 585/408; 585/640; 585/733
[58] Field of Search .................... 585/408, 640, 733

[56] References Cited

U.S. PATENT DOCUMENTS

| | | | |
|---|---|---|---|
| 3,931,349 | 1/1976 | Kuo | 260/668 |
| 3,998,899 | 12/1976 | Daviduk et al. | 260/609 |
| 4,044,061 | 8/1977 | Chang et al. | 260/668 |
| 4,387,263 | 6/1983 | Vogt et al. | 585/640 |
| 4,404,414 | 9/1983 | Penick et al. | 585/469 |
| 4,418,236 | 11/1983 | Cornelius et al. | 585/408 |

Primary Examiner—Curtis R. Davis
Attorney, Agent, or Firm—Alexander J. McKillop; Michael G. Gilman; L. G. Wise

[57] ABSTRACT

A catalytic conversion process for reacting lower aliphatic $C_1$-$C_4$ oxygenates, such as methanol, to produce gasoline boiling range hydrocarbons. Improved cycle average gasoline yield is sustained without a substantial reduction in cycle average gasoline octane number by selectively programming the conversion reactor inlet temperature during a process cycle.

16 Claims, 4 Drawing Sheets

REACTOR TEMPERATURE PROGRAMMING

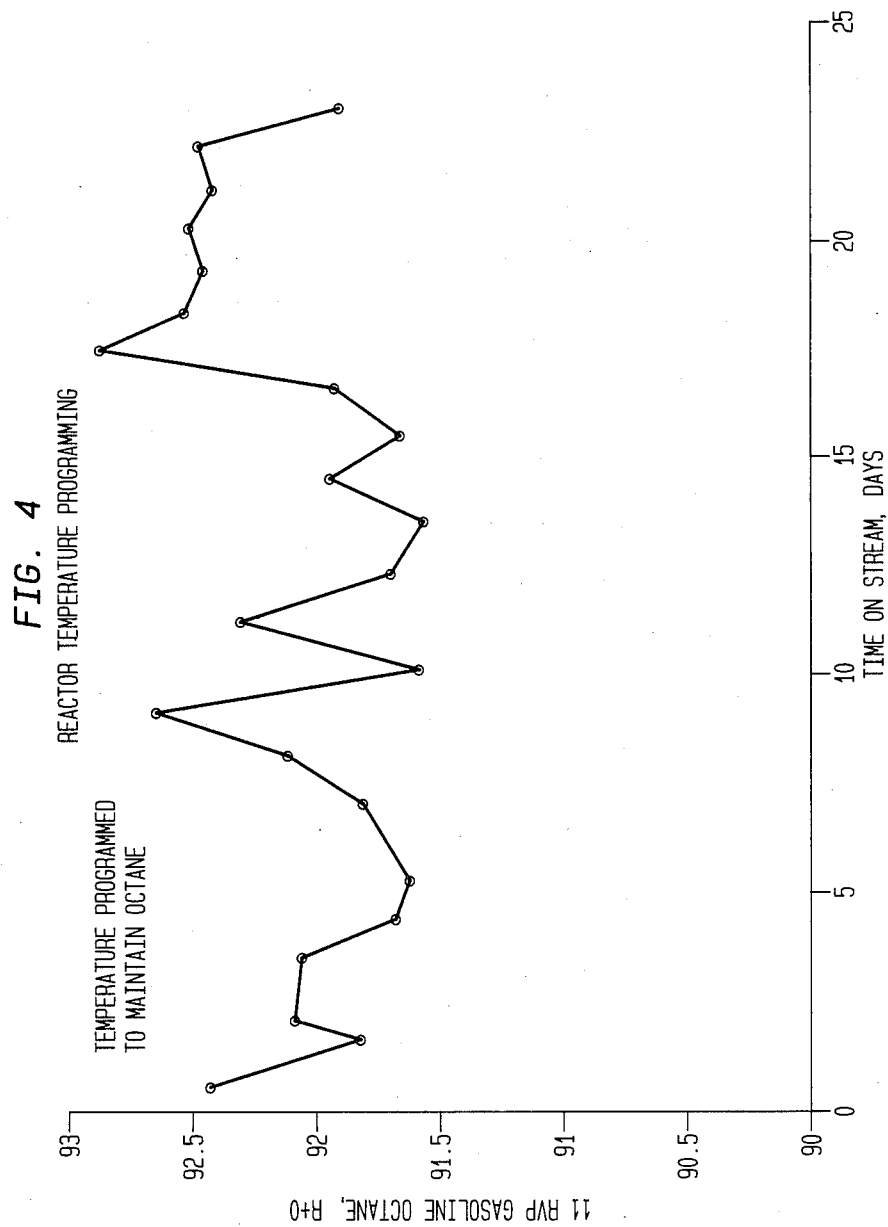

CONVERSION OF OXYGENATES TO GASOLINE AT VARIABLE INLET TEMPERATURE

FIELD OF THE INVENTION

The present invention relates to the synthetic production of gasoline. More particularly, the present invention relates to a process for converting lower aliphatic $C_1$-$C_4$ oxygenates, such as methanol, to gasoline with improved yields by inlet temperature programming without experiencing a decreasing value in gasoline octane number.

BACKGROUND OF THE INVENTION

The conversion of methanol to hydrocarbon products may take place in a fluidized bed process as described, for example, in U.S. Pat. Nos. 4,071,573 and 4,138,440, or in a fixed bed as described in U.S. Pat. Nos. 3,998,899, 3,931,349 and 4,035,430. In the fixed bed process, the methanol is usually first subjected to a dehydrating step, using a catalyst such as gamma-alumina, to form an equilibrium mixture of methanol, dimethylether (DME) and water. This mixture is then passed over a conversion to the hydrocarbon products which are mainly in the range of light gas to gasoline. The water may be removed from the methanol dehydration products prior to conversion to hydrocarbons as may the methanol which can be recycled to he dehydration step, as described in U.S. Pat. No. 4,035,430. Removal of the water is desirable because the catalyst may tend to become deactivated by the presence of the water vapor at the reaction temperatures employed, but this step is by no means essential.

In the operation of the fixed bed process, a major problem which has to be dealt with is the thermal balance. Although the conversion reaction is highly energy efficient, the conversion of the oxygenated feed stream (methanol, DME) to the hydrocarbons is a strongly exothermic reaction liberating approximately 1480 kJ. (1400 Btu) of heat per kilogram of methanol. In an adiabatic reactor this would result in a temperature rise which would lead to extremely fast catalyst aging rates or even to damage to the catalyst. Furthermore, the high temperatures which might occur could cause undesirable products to be produced or the product distribution could be unfavorably changed. For instance, it is known that increases in reactor temperature result in a reduction in gasoline yields, albeit at an increase in gasoline octane. Therefore, close control of the conversion temperature has been found to be highly important to avoid a loss in gasoline yields. A degree of control over the temperature of the catalyst bed can be achieved by suitable choice of bed configuration but this expedient is generally insufficient by itself and other methods must be employed. One particularly efficacious method is to employ a light gas portion of the hydrocarbon product as recycle, as described in U.S. Pat. No. 3,931,349, which patent is incorporated herein by reference in its entirety.

Recycling of process gas limits the temperature rise across the catalyst bed to less than 94° C. (200° F.). Also during the reaction, a small amount of hydrocarbon is deposited on the catalyst as coke, requiring periodic catalyst regeneration. Operation of the process, however, is continuous because additional reactors, arranged in parallel, permit an individual reactor to swing from operation to regeneration. The final gasoline yield from the fixed bed process, after alkylating the light olefins formed, is about 85–90 percent by weight of the total hydrocarbons formed. The remaining hydrocarbons are available, mostly as liquid petroleum gas (LPG) and a small amount of fuel gas.

The conversion of oxygenates is described in depth by C. D. Chang, Catal. Rev.-Sci. Eng., 25, 1(1983) and in U.S. Pat. No. 4,404,414 to Penick et al. These references are incorporated herein in their entirety.

The continuing effort of research workers in the MTG field to improve the process have focused on improvements in gasoline yield as one opportunity. The MTG process is noteworthy for producing good yields of gasoline, above 80% on a cycle average basis. Yet, more noteworthy is the fact that the yields are of an aromatic-rich gasoline with good octane number values. The research challenge, then, is to improve process average cycle yields of gasoline, but without sacrificing gasoline quality as measured by octane number. Investigations heretofore have established what appeared to be inextricable relationships between gasoline yield and octane number such that changes in process conditions leading to an improvement in average gasoline cycle yield were achieved at the expense of product quality as represented by octane number.

In addition to the management of the high exotherm associated with the conversion of oxygenates to gasoline, another factor that restricts and complicates research toward improvements in gasoline yield for the MTG process is the requirement that the process operate at or near quantitative oxygenates conversion. Less than quantitative conversion, referred to as "methanol breakthrough," presents severe problems in waste disposal and/or methanol recovery from aqueous streams, which quickly leads to punishing economic penalties for the process and, therefore, is to be avoided. Accordingly, whatever advances research workers are to make in MTG process yield improvement must be made while maintaining essentially quantitative conversion of methanol.

Research leading to the discovery of the present invention has been directed to programming the temperature of the conversion reaction. In U.S. Pat. No. 4,387,263 to Vogt temperature increasing is used in the conversion of methanol to olefins. The patent is directed to a process for making $C_2$ to $C_4$ olefins from gas mixtures containing methanol, dimethylether and optionally steam in the presence of catalysts at temperatures of 250° to 500° C. under pressures of 0.1 and 6 bars. This patent further describes controlling the temperature during the conversion reaction of the methanol-containing feedstock to assure a constant conversion of at most 80% conversion of methanol to hydrocarbons by increasing the temperature during the conversion process to compensate for loss of catalytic activity over time onstream. One example in this patent states that the initial conversion temperature is about 280° C. and is increased up to 360° C. during the gradual loss of catalytic activity. However, although this patent generally discloses increasing the temperature of the feed in the conversion zone in a process seeking olefins to insure a constant conversion proportion of methanol to hydrocarbons, this type of process is quite different from the improved MTG process of the present invention. that is, the MTG process operates at much higher pressrres, i.e., about 10–40 bars, and operates at a 100% conversion level. Moreover, U.S. Pat. No. 4,387,263 seeks an entirely different product,i.e., olefins, than the gasoline boiling range materials of the MTG process. Thus, the type of temperature control used to compensate for loss of catalytic activity in this patent would in no way suggest that temperature programming the MTG conversion reactor inlet temperature would significantly improve cycle average gasoline yield in the MTG process without substantial reduction in cycle average octane number.

It is one object of the present invention to significantly improve the cycle average gasoline yield in the MTG process.

Another object of the present invention is to significantly improve the life of the conversion catalyst in the MTG process, without suffering a substantial reduction in cycle average gasoline octane number.

A further object of the present invention is to improve the MTG process from an economical standpoint by improving cycle average gasoline yields without a concomitant reduction in cycle average octane number.

SUMMARY OF THE INVENTION

These and other objects of the present invention are satisfied by programming or varying the conversion reactor inlet temperature during a process cycle. More specifically, in one aspect of the present invention, these objects are attained by selectively increasing the conversion reactor inlet temperature after methanol breakthrough occurs during the cycle. Further, in another aspect of the present invention, temperature programming does not have to be implemented at methanol breakthrough, but may be conducted in such a manner so as to maintain gasoline octane at a constant level.

The objects of the invention may further be met by programming the conversion reactor inlet temperature by an amount just sufficient to maintain essentially quantitative conversion of oxygenates such as methanol.

The invention comprises a process for converting lower aliphatic oxygenates hydrocabbon feedstock to aromatic-rich gasoline range hydrocarbons comprising, contacting the feedstock with a fixed bed of acidic shape selective medium pore zeolite conversion catalyst particles at elevated inlet temperature under conversion conditions sufficient to provide essentially quantitative conversion of said feedstock. The inlet temperature is increased incremetally during the process cycle by an amount just sufficient to maintain essentially quantitative conversion of said feedstock until the process cycle is terminated coincident with the loss of essentially quantitative feedstock conversion. In the practice of the present invention as described, improved yields of gasoline range hydrocarbon products are realized. But most surprisingly, these improved yields are realized without a corresponding loss in octane number for the gasoline so produced.

BRIEF DESCRIPTION OF THE FIGURES

FIGS. 2, 3 and 4 are graphs plotting the experimental results obtained as to the increase in cycle average gasoline yield when the conversion reactor inlet temperature is programmed so as to maintain octane constant during a process cycle.

DETAILED DESCRIPTION OF THE INVENTION

Figure 1:
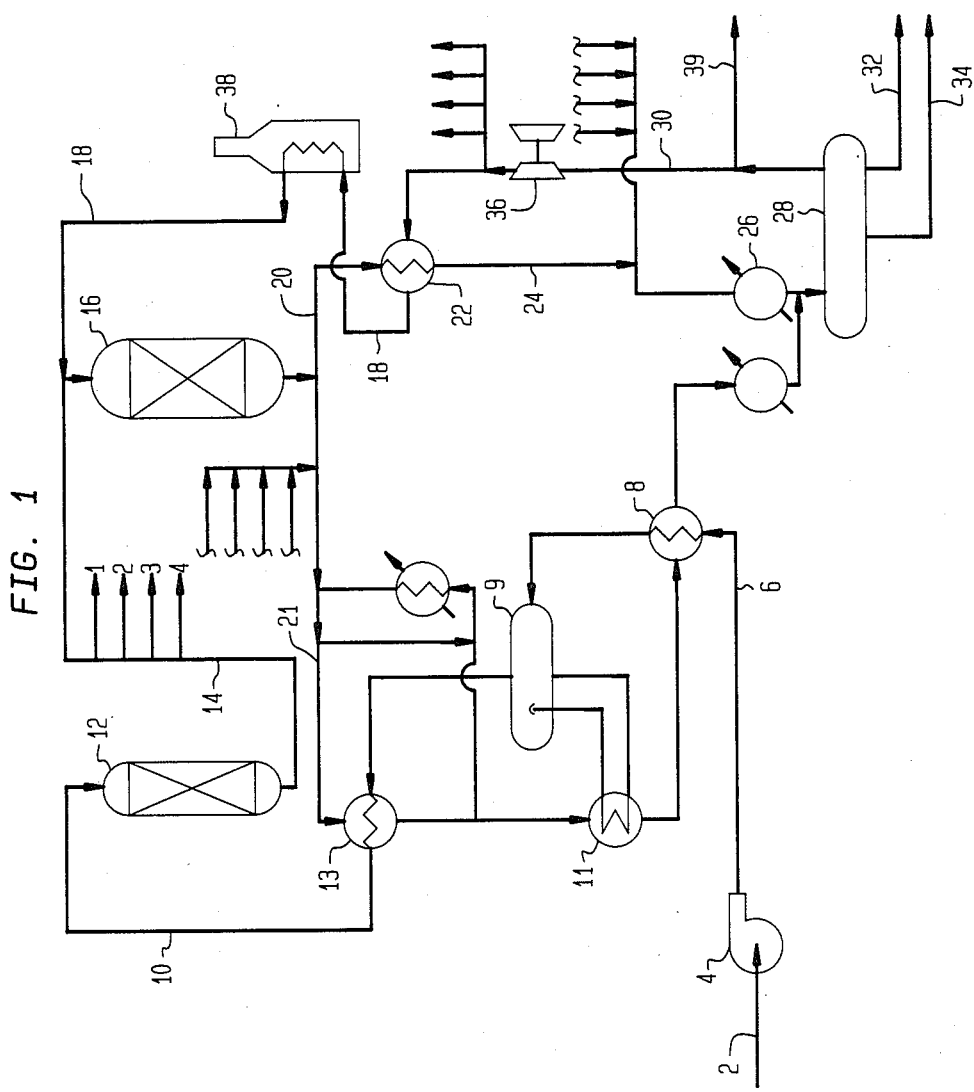
FIG. 1 represents a standard fixed-bed MTG process configuration which may be used in accordance with the present invention.

The known MTG process normally is operated at a constant conversion reactor inlet temperature throughout a process cycle. Process variable studies have shown that increases in conversion reactor temperature reduce gasoline yields and increase gasoline octane, and vice-versa. However, it has now been unexpectedly determined that if the MTG conversion reactor inlet temperature is selectively programmed during a process cycle, it is possible to significantly improve cycle average gasoline yield without suffering a substantial reduction in the cycle average gasoline octane number.

Starting Materials

The present process is useful for the conversion of a number of differing oxygenated organic compounds into hydrocarbon products. The process is useful for the conversion of aliphatic compounds including lower alcohols such as methanol, ethanol and propanol, ethers such as DME and diethyl ether, ketones such as acetone, methyl ethyl ketone, aldehydes such as acetaldehyde, esters such as methyl formate, methyl acetate and ethyl acetate, carboxylic acids such as acetic acid, bulyric acid and their anhydrides e.g., acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions. The product in each case will be a hydrocarbon mixture ranging from light gas to heavier fractions ($C_{10+}$) but will generally be concentrated in the gasoline boiling range ($C_5$-220° C.). The process is particularly useful in the catalytic conversion of methanol to hydrocarbons in the gasoline boiling range and, for convenience, the process will be described below with reference to such a process although it should be remembered that the principles are applicable to a broader range of conversion, as set out above.

If methanol is used as the starting material for the process it is preferred to subject it to an initial dehydration step to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred. It is possible to dehydrate only part of the methanol with, for example, the dehydration product going to one reactor and the raw methanol going to another.

Because the oxygenated charge may be fed into the reactors in different forms, e.g., methanol and DME, it will often be convenient, for purposes of calculating recycle ratio and other factors, to base the calculations upon a single equivalent charge. For example, if both methanol and DME are fed to the reactors, the total charge may be reduced to a basis of "methanol equivalents" in which one mole of DME is equal to two methanol equivalents. Thus, the reactant flow at any point may be readily reduced to a single value from which other may be derived, e.g., recycle ratio.

Process Outline

The conversion of methanol or methanol equivalents to gasoline is accomplished in contact with zeolite catalysts, such as ZSM-5, usually quantitatively in the presence of active catalyst. In addition to gasoline and other hydrocarbons, water is a reaction by-product. As previously noted, the reaction is highly exothermic and the exothermic character of the conversion reaction requires careful management of the recycle ratio. "Methanol breakthrough," a term of art indicating the appearance of methanol in the aqueous product stream and, therefore, less than quantitative conversion, has generally been followed to signal the end of the process cycle and the need to regenerate catalyst.

The production of even very dilute aqueous methanol product streams presents an operator with costly waste disposal or separation problems and must be avoided. Accordingly, when any combination of process parameters produces a methanol conversion of less than 99%, or more typically 99.9%, the cycle under those conditions is ended, largely for economic reasons.

Referring now to FIG. 1 a typical process flow diagram of the MTG process is presented. Crude methanol in a liquid phase condition is charged to the process by conduit 2 communicating with pump 4. The methanol is pressured to about 2500 kPa (350 psig) in pump 4 and then passed by conduit 6 to heat exchanger 8 wherein the liquid methanol is preheated. It is then passed into drum 9 where it is vaporized at about 185° C. (400° F.) by indirect heat exchanger 11. The methanol is then superheated in indirect exchanger 13 to about 315° C. (600° F.) and it is passed by conduit 10 to the inlet of the dimethyl ether forming catalytic reactor 12. In catalyst contained in reactor 12, a fixed bed of gamma alumina catalyst is maintained as a fixed bed of catalyst through which the methanol reactant passed downwardly through or as an annular bed of catalyst for radial flow of reactant material therethrough. A single down-flow fixed catalyst bed or a plurality of separate fixed down-flow catalyst beds are arranged for converting the methanol feed under restricted temperature conditions as herein described to essentially an equilibrium product comprising methanol, dimethyl ether and water at a temperature of about 395°–415° C. (740°–780° F.) due to the exothermic temperature rise catalytically generated in the operation. The equilibrium product thus obtained may be construed as an ether rich product which is then passed by conduit 14 to a second reactor stage 16 housing one or more separate parallel sequentially arranged beds of a ZSM-5 type of crystalline zeolite.

A diluent material introduced by conduit 18 is combined with the ether rich effluent obtained as hereinbefore discussed before contact of the mixture is made with the HZSM-5 crystalline zeolite catalyst under heat generating or exothermic reaction conditions controlled to restrict the temperature increase between the reactor inlet and reactor outlet not to exceed about 111° C. (200° F.) and preferably not to exceed about 83° C. (150° F.). The conversion of the ether rich effluent by the HZSM-5 catalyst is highly exothermic as discussed above and controlled within desired limits by use of gasiform heat dissipating diluent material. During this highly exothermic operation the ether rich effluent or equilibrium mixture comprising dimethyl ether, methanol and water is controlled to effect the conversion thereof to gasoline boiling range components comprising aromatic and isoparaffins. The aromatic components comprising benzene, toluene and xylene are preferred components over the higher boiling durene aromatic material and efforts are made (e.g.,reactant partial pressure, and reactant plug flow operation) to promote this end.

The product effluent of the HZSM-5 reaction zone 16 is passed through one or more cooling steps to reduce the temperature to a desired low temperature. In the specific arrangement of the figure the effluent is passed by conduit 20 to heat exchanger 22 wherein the effluent temperature is reduced to about 94° C. (200° F.) by indirect heat exchange with diluent material removed therefrom by conduit 18. The diluent will be at a temperature of about 315°–343° C. (600°–650° F.). The partially cooled effluent is removed f exchanger 22 and passed by conduit 24 to cooling water and/or air heat exchanger 26 wherein a furteer cooling of the effluent to about 38° C. (100° F.) is accomplished. Some of the effluent is passed via conduit 21 to heat exchangers 13,11, and 8 to superheat, vaporize, and preheat, respectively, the methanol feed. The effluent from exchanger 8 is cooled in exchanger 26 and combined with cooled effluent from reactor conduit 20 and passed into separator 28, where liquid hydrocarbon, liquid water and gaseous material are separated. In the arrangement of the drawing, most of the gaseous effluent is then passed by conduit 30 to heat exchanger 22 where it is again passed in indirect heat exchange with reactor effluent and finally heater 38 before entering reactor 16. Water product is removed from separator 28 via conduit 34 for further treatment. Liquid hydrocarbon product is removed from separator 28 via conduit 32 and is sent to a product recovery section (not shown). Of course many other heat exchange arrangements may be provided for reducing the reactor effluent temperature from about 426° C. (800° F.) to about 38° C. (100 degrees F.) before passage to separator 28. Separator 28 is maintained at a temperature of about 38° C. (100° F.) and a pressure of about 1540 kPa (220 psig). In the separator a rough cut is made between gasiform diluent materials, desired aromatic and isoparaffin product and water. Water is withdrawn by conduit 34. A gasiform product material lower boiling than desired gasoline boiling range constituents is withdrawn by conduit 30 and passed to a compressor 36. A plurality of parallel arranged gas compressors may be used for this purpose. The gasiform material is compressed by compressor 36 to a pressure of about 2310 kPa (330 psig) before passage to exchanger 22. Excess gas is removed via conduit 39 and sent to product recovery. Inlet temperatures to the first reactor are normally about 300° C. (570° F.) to 400° C. (750° F.) but preferably about 330° C. (625° F.) to 370° C. (700° F.).

In the present invention, inlet temperatures are varied by increasing to maintain essentially quantitative methanol conversion. Temperatures may be increased continuously in amount less than about 1 degree per day or temperatures may be increased in stages by increments of about 2° to 15° C. (3° to 30° F.), but preferably in stages of about 3° to 9° C. (5° to 20° F.).

Weight hourly space velocity of methanol to the conversion reactor, i.e., weight of total oxygenate charge equivalent basis to weight of catalyst per hour is normally kept between the range of 10.0 to 0.1, but preferably 5 to 0.5 WHSV.

However, in one embodiment of the present invention WHSV is varied in combination with increasing temperature wherein the combination achieves a surprising improvement in cycle average gasoline yield without loss of octane number. WHSV may be varied from a high value above average WHSV to a low value while increasing inlet temperature incrementally so as to maintain essentially quantitative methanol conversion.

The conversion of methanol or methanol equivalents is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica: alumina ratio is correctly determined.

Preferred zeolites which have the specified values of Constraint Index and silica:alumina ratio include zeolites ZSM-5, ZSM-11, ZSM-12, ZSM-35, and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), and European Patent Publication No. 15132, and reference is made to these patents for details of these zeolites, their preparation and properties. Of these zeolotes, ZSM-5 is preferred.

The zeolite catalyst used is at least partly in the hydrogen form e.g. HZSM-5 but other cations e.g. rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g. by heating at over 500 degrees C. for 1 hour or more. The hydrogen form can then be obtained by base exchange with ammonium salts followed by calcination e.g. at 500 degrees C. in air. Other cations e.g. metal cations can be introduced by conventional base exchange techniques.

Specific Embodiments

In the conventional MTG process, upon the onset of "methanol breakthrough," the normal practice is to terminate the cycle and regenerate the conversion catalyst. The present invention is characterized, in one aspect, in that instead of regenerating the conversion catalyst such as ZSM-5 by controlled combustion of the coke on the catalyst at methanol breakthrough, the conversion reactor inlet temperature is increased instead, and the cycle is continued until methanol breakthrough occurs again. After the second methanol breakthrough, this sequence is repeated, i.e., the conversion reactor inlet temperature is increased. The data described hereafter in Example 1 evidences the unexpectedly improved cycle average gasoline yield and cycle average octane number obtained in accordance with the selective conversion reactor inlet temperature programming described above. The improved yields are observed in the process of the present invention upon increasing the conversion reactor inlet temperature once upon reaching methanol breakthrough during a process cycle or increasing the inlet temperature repeatedly.

Further, another aspect of the present invention resides in the selective programming of the conversion reactor inlet temperature such that the gasoline octane, R+O, remains constant throughout a process cycle. This type of continuous temperature programming of the conversion reactor inlet temperature has also unexpectedly been determined to desirably increase the cycle average gasoline yield. The data described hereafter in Example 2 and FIGS. 2-4 demonstrate this aspect of the present invention.

The term temperature programming as used in the present invention means generally increasing the conversion reactor inlet temperature above the normal inlet temperature, e.g., 640 degrees F., in either a stepwise or continuous manner in an amount sufficient to maintain essentially quantitative methanol conversion and maintain essentially constant octane number, or by an amount sufficient to maintain constant octane number while improving average cycle yield.

The above-described improvements to the basic fixed-bed MTG process are hereafter illustrated by reference to the following specific examples. However, these examples should not be construed as limiting the scope of the present invention in any manner whatsoever.

Example 1

A fixed-bed MTG process is operated in a configuration as shown in FIG. 1 with a dehydration reactor containing gamma-alumina catalyst followed by a conversion reactor containing ZSM-5 catalyst. As shown in Table 1 below, the process is operated at constant conditions until methanol breakthrough occurs. The initial conversion reactor inlet temperature is 640 degrees F. The feed composition by percent methanol is also shown in Table 1.

At this point, instead of regenerating the ZSM-5 catalyst by controlled combustion of the coke deposited on the catalyst, necessitating taking the feed off-stream, the conversion reactor inlet temperature is increased to 655 degrees F., and the cycle is continued until methanol breakthrough occurs again.

After the second methanol breakthrough, conversion catalyst regeneration by combustion is again not performed, but the conversion reaction inlet temperature is increased to 669 degrees F. and the cycle is continued until methanol breakthrough occurs for the third time.

The data obtained from this process cycle is summarized in Table 1. All process condition information is an average for the time of operation at the indicated conversion reaction inlet temperature. The cycle length is the cumulative cycle length at the indicated conversion reactor inlet temperature. The gasoline yield and octane are cycle averages to the indicated conversion reaction inlet temperature.

TABLE 1

| Conv. Rx Inlet Temp., °F.(°C.) | 640(338) | 655(346) | 669(354) |
|---|---|---|---|
| Pct Methanol in Charge, Wt % | 86.4 | 86.5 | 86.8 |
| Pressure, psig | 300 | 300 | 300 |
| Dehydration Rx Inlet Temp. °F.(°C.) | 600(315) | 601(316) | 601(316) |
| Conv. Rx Methanol WHSV | 1.6 | 1.6 | 1.6 |
| Recycle Ratio, mol/mol charge | 7.2 | 7.1 | 7.2 |
| Cycle Length to Indicated Conv. Rx Inlet Temp., days | 16.8 | 28.7 | 34.7 |
| Cum. Avg 11 RVP Gaso. Yield, Wt % HC | 89.1 | 89.6 | 89.7 |
| Cum. Avg 11 RVP Gaso. Octane, R + O | 91.6 | 91.7 | 91.8 |

As shown in Table 1, operation at 640° F. (338° C.) conversion reactor inlet temperature results in a cycle length of 16.8 days, and 11 RVP gasoline yield and octane average 89.1 weight percent of hydrocarbons and 91.6 R+O, respectively. Upon increasing the conversion reactor inlet temperature to 655° F.(346° C.), cycle length is increased to 28.7 days, and cycle average (through 28.7 days) gasoline yield and octane increased to 89.6 weight percent and 91.7 R+O, respectively. Similar behavior is observed upon programming to a conversion reactor inlet temperature of 669° F.(354° C.)

These significantly improved results as to gasoline yield increase without a decrease in octane are unexpected, since, as noted above, process variable studies have clearly shown that gasoline yield normally decreases upon an increase in reactor temperature during the MTG process. Further, increases in gasoline yield are normally accompanied by decreases in octane. For example, if a whole cycle is continuously operated at a constant conversion reactor inlet temperature, the expected behavior in gasoline yield and octane will result. However, if the reactor inlet temperature is selectively programmed in accordance with the present invention when methanol breakthrough occurs, significantly improved cycle average gasoline yields can be obtained, without an undesired decrease in octane.

Example 2

A standard fixed-bed MTG configuration, as shown in FIG. 1, is again operated. The dehydration catalyst is 1/16" gamma-alumina (39.7 g), and the conversion catalyst is ZSM-5 (112 g). Process conditions are as follows:

| Feed MeOH/Water, wt/wt | | 86/14 |
|---|---|---|
| Dehydration Rx Inlet Temperature, | °F. | 600 |
| | (°C.) | 315 |
| Dehydration Rx Outlet Temperature, | °F. | 760 |
| | (°C.) | 405 |
| Conversion Rx Inlet Temperature, | °F. | 639–680 |
| | (°C.) | 337–360 |
| Conversion Rx Outlet Temperature, | °F. | 754–797 |
| | (°C.) | 401–425 |
| Pressure, psig | | 300 |
| Conversion Rx MeOH WHSV, g/g cat-hr | | 1.6 |
| Recycle Ratio, mol/mol feed | | 7/1 |

In this Example, the conversion reactor inlet temperature is programmed throughout the process cycle so that the octane of the 11 RVP gasoline product is maintained at a constant level. The process is terminated when methanol conversion declined to less than 99.9%, i.e., at methanol breakthrough.

Figure 2:
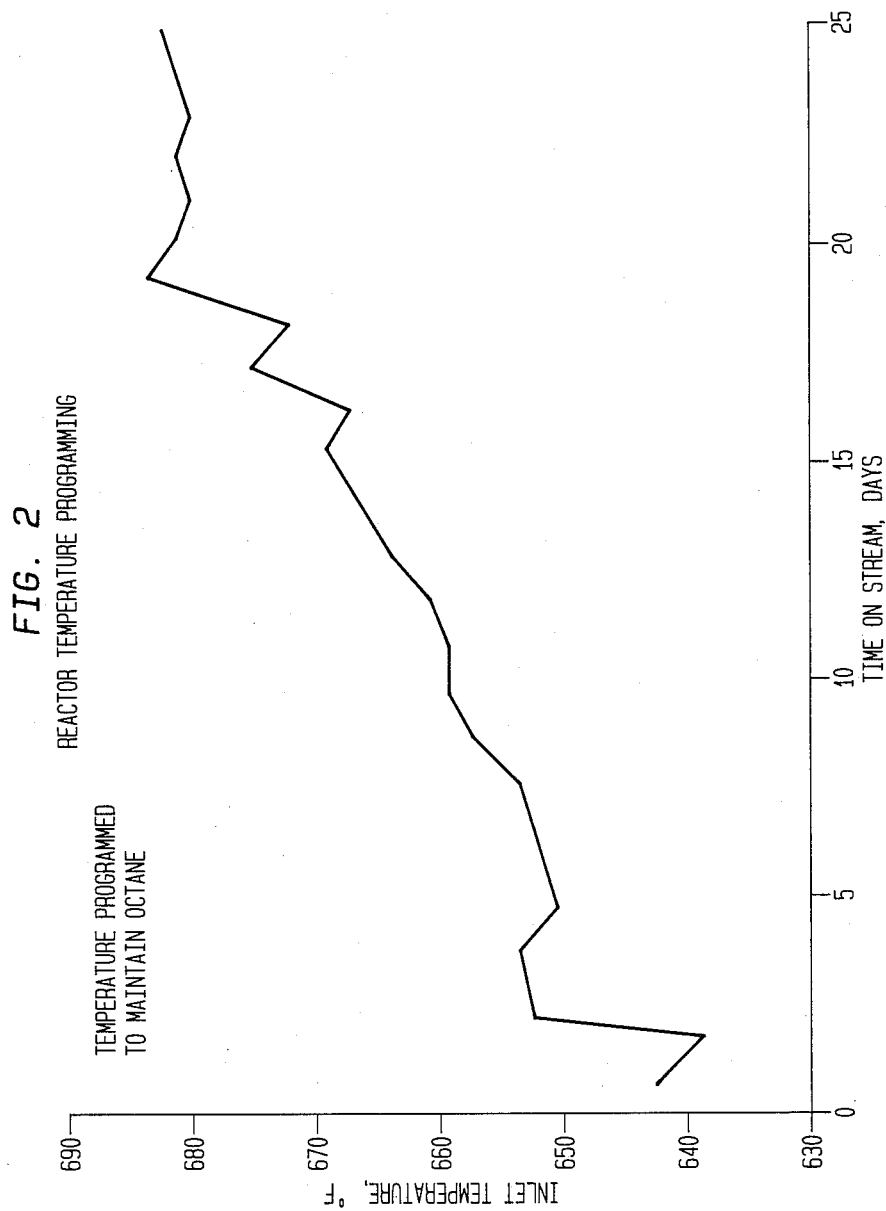
Figure 3:
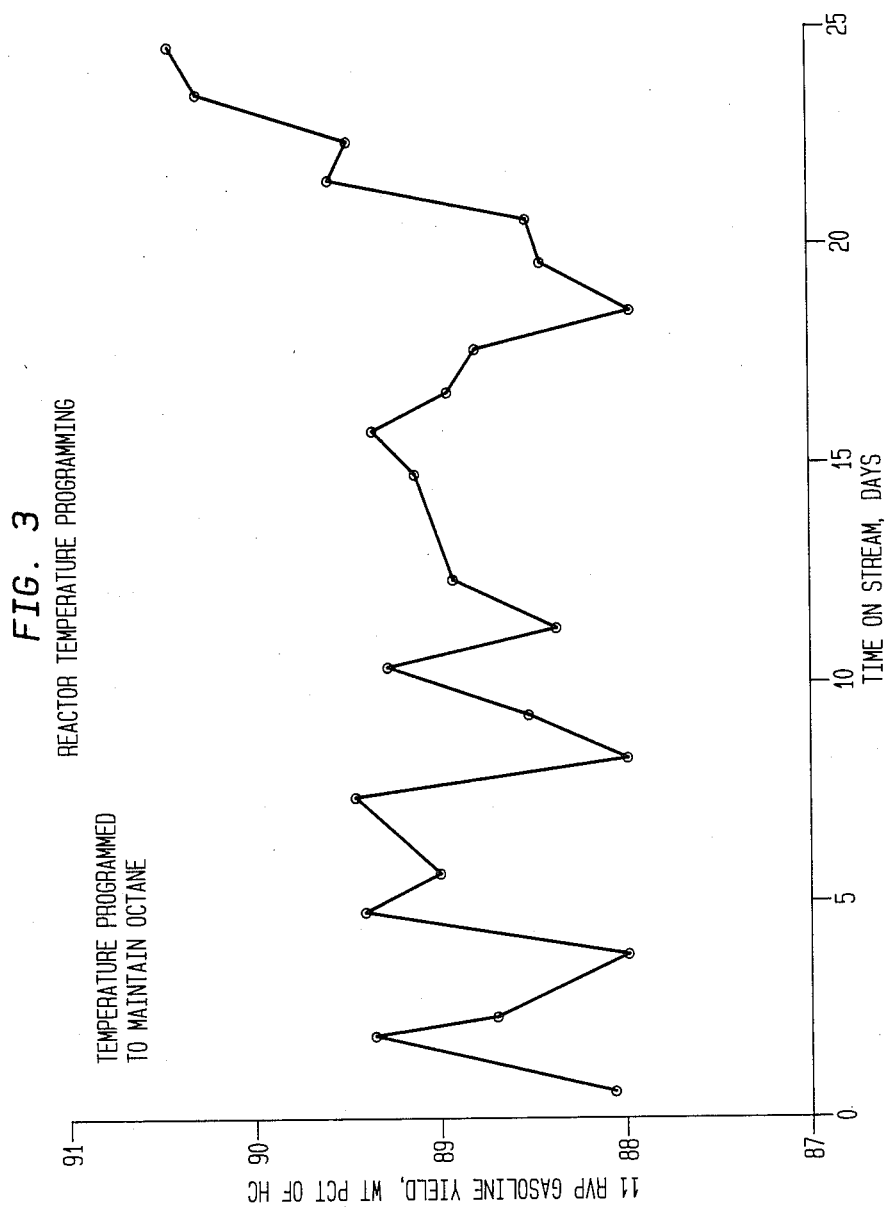

The conversion reactor inlet temperature programming policy which is employed during this run is shown in FIG. 2 for a time on-stream of 25 days. The gasoline yield obtained is shown in FIG. 3, and the corresponding octane is shown in FIG. 4. As is clearly seen from FIG. 4, gasoline octane would have decreased without the corresponding temperature programming shown in FIG. 2. The resulting 11 RVP cycle average gasoline yield and octane, averaged over the whole cycle is 88.8 wt % hydrocarbons and 92.0 R+O, respectively.

Having thus generally described the process of the present invention and discussed specific embodiments in support thereof, it is to be understood that no undue restrictions as to the scope of the present invention are to be imposed by reason thereof.

What is claimed is:

1. In a process for converting at least 99.9% of $C_1$–$C_4$ oxygenates to primarily $C_5+$ gasoline boiling range hydrocarbons with a crystalline zeolite conversion catalyst, the improvement which comprises, selectively programming a conversion reactor inlet temperature during a process cycle so as to increase cycle average gasoline yeld without a substantial reduction in cycle average gasoline octane number.

2. The process of claim 1, wherein said programming comprises increasing the conversion reactor inlet temperature at oxygenate breakthrough by an amount effective to increase cycle average gasoline yield.

3. The process of claim 1, wherein said programming comprises adjusting the conversion reactor inlet temperature such that gasoline octane remains constant during the process cycle.

4. A process for converting at least 99.9% of lower aliphati oxygenated hydrocarbon feedstock to primarily $C_5+$ aromatic-rich gasoline range hydrocarbons comprising to step of:

(a) contacting the feedstock with a fixed bed of acidic shape selective medium pore zeolite conversion catalyst particles at elevated inlet temperature under conversion conditions sufficient ot provide essentially quantitative conversion of siad feedstock;

(b) increasing said inlet temperature incrementally during the process cycle by an amount just sufficient to maintain at least 99.9% conversion of said feedstock;

(c) terminating the process cycle when feedstock conversion falls below 99.9%, whereby an improved cycle aveavrage gasoline yield is achieved at high octane value.

5. The process of claim 4 wherein the inlet temperature is increased stepwise in increments of between about 5 and 20° F.(3 to 9° C.)

6. The process of claim 4 wherein the inlet temperature is increased in increments between 600 and 700 degrees F. (315° and 370° C.).

7. The process of claim 4 wherein the gasoline product octane value is maintained essentially constant during the cycle.

8. The process of claim 4 wherein the feedstock comprises methanol, dimethyether or mixtures thereof; wherein the zeolite catalyst comprises an aluminasilicate having a silica to alumina ratio of at least 12 and a constraint index of about 1 to 12.

9. The process of claim 4 wherein the catalyst is HZSM-5.

10. The process of claim 4 wherein the conversion conditions comprises a feedstock feedrate WHSV based on catalyst between 10 and 0.1.

11. The process of claim 10 wherein said WHSV is varied continuously or in stages from a high WHSV to a lower WHSV.

12. A process for converting at least 99.9% of lower aliphatic oxygeanted hydrocarbon feedstock to primarily $C_5+$ aromatic-rich gasoline range hydrocarbons comprising the step of:

(a) contacting the feedstock with a fixed bed of acidic shape selective medium pore zeolite conversion catalyst particles at elevated inlet temperature under conversion conditions sufficient to produce said gasoline;

(b) increasing the inlet temperature incrementally during the process cycle while maintaining essentially constant octane value for the gasoline produced;

(c) terminating the process cycle coincident with either the degradation of gasoline product octane value or a reduction in feedstock conversion below 99.9%, whereby improved cycle average gasoline product yields are achieved.

13. The process of claim 12 wherein the inlet temperature is increased stepwise in increments of between about 5 and 20 degrees F.(3° and 9° C.) and varying WHSV between 10 and 0.1.

14. The process of claim 12 wherein the inlet temperature is increased in increments between 600 and 700 degrees F.

15. The process of claim 12 wherein the feedstock comprises methanol, dimethylether or mixtures thereof; wherein the zeolite catalyst comprises an aluminasilicate having a silica to alumina ratio of at least 12 and a constraint index of about 1 to 12.

16. The process of claim 12 wherein the catalyst is HZSM-5.

* * * * *